United States Patent [19]

Atsumi et al.

[11] 4,317,825
[45] Mar. 2, 1982

[54] ANTITUMOR AND IMMUNOSUPPRESSIVE 4-CARBAMOYL IMIDAZOLIUM-5-OLATE DERIVATIVES

[75] Inventors: Toshio Atsumi, Kawanishi; Tetsutaro Sanjiki, Ibaraki; Takao Kiyohara, Takarazuka, all of Japan

[73] Assignee: Sumitomo Chemical Company, Limited, Osaka, Japan

[21] Appl. No.: 175,688

[22] Filed: Aug. 5, 1980

[30] Foreign Application Priority Data

Aug. 8, 1979 [JP] Japan .................... 54-101684
Apr. 4, 1980 [JP] Japan .................... 55-45042

[51] Int. Cl.$^3$ ............. A61K 31/415; A61K 31/495; C07D 409/12; C07D 405/12
[52] U.S. Cl. ................... 424/250; 424/266; 424/270; 424/273 R; 544/405; 546/278; 548/105; 548/110; 548/201; 548/214; 548/336; 548/337
[58] Field of Search ............. 546/278; 548/336, 337, 548/201, 214; 544/405; 424/273 R, 266, 270, 250

[56] References Cited

U.S. PATENT DOCUMENTS

| | | | |
|---|---|---|---|
| 3,033,867 | 5/1962 | Gordon et al. | 546/97 |
| 4,140,788 | 2/1979 | Atsumi et al. | 548/301 X |
| 4,160,098 | 7/1979 | Möller et al. | 548/336 X |
| 4,218,457 | 8/1980 | Atsumi et al. | 546/278 X |
| 4,260,774 | 4/1981 | Atsumi et al. | 548/336 |

FOREIGN PATENT DOCUMENTS 50-121276 9/1975 Japan .
53-5162 1/1978 Japan .
53-53652 5/1978 Japan .

OTHER PUBLICATIONS

Sakaguchi, K., et al., *J. Antibiotics*, 28, 798–803 (1975).
Mizuno, K., et al., *J. Antibiotics*, 27, 775–782 (1974).
Schipper, E., et al., *J. Am. Chem. Soc.*, 74, 350–353 (1952).
Tsujino, M., et al., *Proc. 1st. Int. Cong. IAMS*, 3, 441–443 (1974).
Miller, C., *J. Am. Chem. Soc.*, 74, 2892–2894 (1952).
Sakaguchi, K., et al., *Cancer Research*, 35, 1643–1648 (1975).
Sakaguchi, K., et al., *Proc. 1st Int. Cong. IAMS*, 3, 539–541 (1974).

*Primary Examiner*—Richard A. Schwartz
*Attorney, Agent, or Firm*—Wenderoth, Lind & Ponack

[57] ABSTRACT

There are provided compounds of the formula:

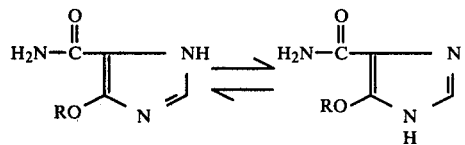

wherein R is a heteroaroyl group containing a nitrogen, sulfur or oxygen atom which may be substituted with a lower alkyl group, an aralkyl group, an acyl group or a halogen atom; or a cycloalkanoyl group which may be substituted with a lower alkyl group, a lower alkenyl group, a halogen atom, a halogeno-lower alkenyl group, a phenyl group, a halogenophenyl group, a lower alkoxyphenyl group, a lower alkylphenyl group, a formyl group, a hydroxy group, an amino group, a carboxyl group, an aminomethyl group or an oxo group, its non toxic salt and a process for producing them. These compounds are useful as antitumor agents and immunosuppressants.

23 Claims, No Drawings

ANTITUMOR AND IMMUNOSUPPRESSIVE 4-CARBAMOYL IMIDAZOLIUM-5-OLATE DERIVATIVES

The present invention relates to novel 4-carbamoylimidazolium-5-olate derivatives and preparation thereof. More particularly, the present invention pertains to 4-carbamoylimidazolium-5-olate derivatives useful as antitumor agents and immunosuppressants, a pharmaceutical composition containing at least one of them and a process for preparing them.

It has been known that the compounds of the following formula (IV) have antitumor and immunosuppressive activity (Japanese Patent Publication (Kokai) Nos. 53-5162, 53-53652),

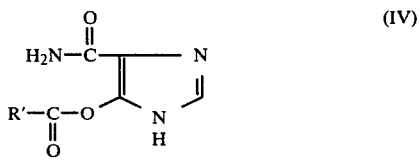

wherein R' is an alkyl group, an adamantyl group or a phenyl group which may be substituted with an alkyl group, an alkoxy group, an alkylthio group, a halogen atom, a nitro group, a cyano group, a methylenedioxy group or an acetamido group.

The compounds of the formula (IV) are practically insoluble in aqueous media, therefore their use in therapy may be restricted.

We have carried out an extensive study seeking new derivatives which are soluble in aqueous media and have now found the novel imidazole derivatives of the present invention.

The novel imidazole derivatives of the present invention are those represented by the following formula (I),

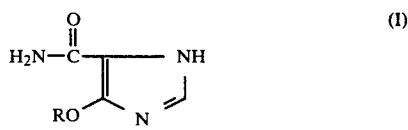

wherein R is a heteroaroyl group containing a nitrogen, sulfur or oxygen atom which may be substituted with a lower alkyl group, an aralkyl group, an acyl group or a halogen atom; or a cycloalkanoyl group which may be substituted with a lower alkyl group, a lower alkenyl group, a halogen atom, a halogeno-lower alkenyl group, a phenyl group, a halogenophenyl group, a lower alkoxyphenyl group, a lower alkylphenyl group, a formyl group, a hydroxy group, an amino group, a carboxyl group, an aminomethyl group or an oxo group, and its non toxic salts.

As used herein, the term "heteroaroyl" means a five to six membered heteroaroyl group containing a nitrogen, sulfur or oxygen atom such as furancarbonyl, thiophenecarbonyl, pyrrolecarbonyl, pyridinecarbonyl, pyridinecarbonyl N-oxide, pyrazinecarbonyl, imidazolecarbonyl, pyrazolecarbonyl, thiazolecarbonyl and the like.

The term "substituted heteroaroyl" may preferably include pyridinecarbonyl substituted with a lower alkyl group (e.g. methyl, n-butyl), thiophenecarbonyl substituted with a lower alkyl group (e.g. methyl), pyrrolecarbonyl substituted with a lower alkyl group (e.g. methyl), furancarbonyl substituted with an aralkyl group (e.g. benzyl), furancarbonyl substituted with an acyl group (e.g. acetyl), pyridinecarbonyl substituted with a halogen atom (e.g. chlorine, fluorine), pyridinecarbonyl substituted with an acyl group (e.g. benzoyl).

The term "cycloalkanoyl" means a cycloalkanoyl containing three to eight members in the ring such as cyclopropanecarbonyl, cyclobutanecarbonyl, cyclopentanecarbonyl, cyclohexanecarbonyl, cycloheptanecarbonyl, cyclooctanecarbonyl and the like.

The term "lower alkyl" means a straight or branched alkyl having 1 to 6 carbon atoms (e.g. methyl, ethyl, n-propyl, isopropyl, n-butyl, n-hexyl).

The term "lower alkoxy" means a straight or branched alkoxy having 1 to 6 carbon atoms (e.g. methoxy, ethoxy, n-propoxy, n-butoxy, isobutoxy, t-butoxy, n-hexyloxy).

The term "halogen" means fluorine, chlorine, bromine and iodine.

The term "aralkyl" means an aralkyl having 7 to 8 carbon atoms such as benzyl, α-methyl benzyl, phenethyl and the like.

The term "acyl" means lower alkanoyl having 1 to 6 carbon atoms (e.g. acetyl, propionyl) and aroyl (e.g. benzoyl which may be substituted with a lower alkyl group, a lower alkoxy group or a halogen atom as defined above.).

The term "lower alkenyl" means a straight or branched alkenyl having 2 to 6 carbon atoms (e.g. vinyl, allyl, propenyl, hexenyl).

The term "a halogeno-lower alkenyl group" means the above alkenyl group substituted with the above halogen atom (e.g. 2,2-dichlorovinyl).

The term "a halogeno-phenyl group" means a phenyl group substituted with the above halogen atom (e.g. p-chlorophenyl).

The term "a lower alkoxyphenyl group" means a phenyl group substituted with a straight or branched alkoxy group having 1 to 6 atoms (e.g. p-methoxyphenyl).

The term "a lower alkylphenyl group" means phenyl substituted with the above lower alkyl groups (e.g. p-tolyl).

The non-toxic salts of the compounds (I) of the present invention having a nitrogen atom in R may be organic or inorganic acid salts formed with such acids as hydrochloric acid, sulfonic acid, nitric acid, phosphoric acid, p-toluenesulfonic acid, benzenesulfonic acid, methanesulfonic acid, tartaric acid, malic acid, lactic acid, maleic acid, and fumaric acid.

The compound of the formula (I) of the present invention can be prepared by reacting 4-carbamoylimidazolium-5-olate (II),

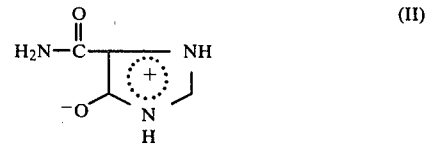

or its reactive derivative with a reactive derivative of carboxylic acids of the formula (III),

wherein R is as defined above.

Examples of preferred reactive derivatives of carboxylic acids of the formula (III) are carboxylic acid halides (e.g. chlorides, bromides, iodides, fluorides), carboxylic acid anhydrides, mixed anhydrides (e.g. mixed anhydrides with ethyl chloroformate, isobutyl chloroformate and the like), activated esters (e.g. p-nitrophenyl ester, ester with N-hydroxysuccinimide), imidazolide (e.g. prepared by reacting N,N'-carbonyldiimidazole with carboxylic acids), activated intermediates prepared by reacting carboxylic acids with reaction products obtained from N,N-dimethylformamide and oxalyl chloride (or phosgene or thionyl chloride or phosphorus pentachloride) and the like.

Examples of preferred reactive derivatives of 4-carbamoylimidazolium-5-olate of the formula (II) are trimethylsilyl derivatives, trialkyltin derivatives, mercury salts, silver salts and the like.

Typical examples of preferred solvents are methylene chloride, chloroform, pyridine, diethyl ether, tetrahydrofuran, dioxane, benzene, toluene, methanol, ethanol, N,N-dimethylformamide, formamide, N,N-dimethylacetamide, acetonitrile, nitromethane, acetone, and ethyl acetate.

The reaction can generally be effected by controlling the reaction temperature at from $-78°$ to $100°$ C., preferably from $-60°$ to $60°$ C.

The reaction of 4-carbamoylimidazolium-5-olate with carboxylic acid halides can usually be carried out in an inert polar solvent or a mixture of water and inert organic solvent preferably in the presence of an inorganic or organic base at a temperature from $-10°$ to $60°$ C. using one to two mole equivalents of acid halides.

Typical examples of said inert polar solvents which may be used in this reaction are tetrahydrofuran, dioxane, pyridine, N,N-dimethylformamide, formamide, N,N-dimethylacetamide and dimethylsulfoxide. Typical examples of said inert organic solvents are tetrahydrofuran, dioxane, diethyl ether, chloroform, dichloromethane, dichloroethane, benzene, toluene, and xylene. Examples of preferred inorganic base are sodium hydroxide, sodium carbonate, sodium bicarbonate, potassium carbonate or bicarbonate and potassium hydroxide. Examples of preferred organic base are pyridine, triethylamine and N,N-dimethylaniline.

The reaction of 4-carbamoylimidazolium-5-olate with activated intermediates prepared by reacting carboxylic acids with reaction products obtained from N,N-dimethylformamide and oxalyl chloride (or phosgene or thionyl chloride or phosphorus pentachloride) can usually be carried out in an organic solvent (e.g. acetonitrile, pyridine, N,N-dimethylformamide, N,N-dimethylacetamide, chloroform) at a temperature from $-78°$ to $80°$ C.

The compounds of the formula (I) can also be prepared by reacting a silylated derivative of 4-carbamoylimidazolium-5-olate with reactive derivatives of carboxylic acids (e.g. acid halides) at a temperature from $-78°$ to $50°$ C. in an inert organic solvent (e.g. dimethylformamide, tetrahydrofuran, dioxane, diethyl ether, benzene, toluene).

The silylated derivative of 4-carbamoylimidazolium-5-olate are known and can be prepared by known methods (Hayashi, et al. Japanese Patent Publication (Kokai) No. 50-121276).

When the compounds of the formula (I) exist in the form of their silylated derivative in the reaction mixture, they can be obtained by a desilylation reaction with desilylation reagents (e.g. acetic acid, methanol).

When the reactive derivative of acid (III) is acid halide, an eliminated halide can be neutralized by an organic base (e.g. triethylamine, pyridine).

The compounds of the formula (I) having cycloalkanoyl group substituted with an amino, hydroxy and carboxyl group can be prepared by the said acylation methods after protecting the amino, hydroxy and carboxyl group with protective groups (e.g. benzyl, benzyloxycarbonyl, t-butoxycarbonyl and the like) and then removing the protective groups.

The compounds of the formula (I) can be isolated and purified by known purification methods (e.g. recrystallization, column chromatography).

The imidazole derivatives of the present invention may exist in a mixture of the two tautomers as follows:

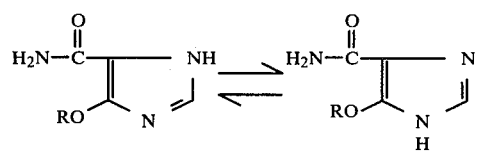

both of which are within the scope of the present invention.

The compounds of the present invention possess potent antitumor activities against Sarcoma 180, Lewis Lung Carcinoma, Ehrlich Carcinoma, P-388 leukemia and the like. The compounds of the formula (I) are useful as antitumor agents and they exhibit particularly excellent inhibiting effects against tumors and prolongation effect of life span.

The antitumor activities of the compounds of the present invention were estimated according to the methods described in "Cancer Chemotherapy Reports" Part 3, Vol. 3 (No. 2) p. 13 (1972). The results are given in the following Table 1.

TABLE 1

| Compound | Antitumor effect on mouse experimental tumors | | |
|---|---|---|---|
| | Dose (mg/kg) Route i.p. | Schedule | Inhibition ratio (%) Lewis Lung Carcinoma (solid) |
| 5-Carbamoyl-1H-imidazole-4-yl furan-2'-carboxylate | 100 | 5q2d | 48.4 |
| 5-Carbamoyl-1H-imidazole-4-yl thiophene-2'-carboxylate | 100 | 5q2d | 62.6 |
| 5-Carbamoyl-1H-imidazole-4-yl isonicotinate | 100 | 5q2d | 41.6 |
| 5-Carbamoyl-1H-imidazole-4-yl N-methylpyrrole-2'-carboxylate | 89.25 | 9qd | 57.3 |
| 5-Carbamoyl-1H-imidazole-4-yl furan-3'-carboxylate | 50 | 9qd | 34 |
| 5-Carbamoyl-1H-imidazole-4-yl 1'-methylcyclohexane-1'-carboxylate | 100 | 5q2d | 60.1 |
| 5-Carbamoyl-1H-imidazole-4-yl cyclobutane-1'-carboxylate | 100 | 5q2d | 33 |

BDF$_1$ male mice, 5 weeks old, weighing between 18 and 22 grams were used. Each test group was composed of 6 to 7 mice. Two million cells of Lewis Lung Carcinoma were injected in the hind leg. The drug was administered intraperitoneally at day 1, 3, 5, 7 and 9 (or 5q2d) or each day from 1 to 9 (or 9qd). After killing the mice at day 13, tumors were removed and weighed. The tumor inhibitory ratio was calculated according to the following formula.

$$\text{Inhibition ratio} = \left(1 - \frac{\text{the mean tumor weights of treated group}}{\text{the mean tumor weights of control group}}\right) \times 100$$

The compounds of the present invention also possess excellent immunosuppressive activity as well as potent antitumor activity.

The compounds (I) of the present invention have low toxicity. They do not show any toxic symptoms, even when over 1000 mg/kg of the compounds are orally administered to a mouse. Moreover, they do not exhibit an influence on decrease of peripheral leucocytes, which is one of the most serious side effects of immunosuppressants.

The compounds of the present invention can be administered orally or parenterally to a warm-blood animal at a daily dose of 2–200 mg/kg as an antitumor agent, and 1–100 mg/kg as an immunosuppressant agent in a conventional dosage unit form.

The compounds of the present invention are made up alone or together with a conventional pharmaceutical carrier or diluent into a conventional solid or liquid pharmaceutical preparation (e.g. powders, granules, tablets, capsules, suspensions, emulsions, solutions) using the conventional methods in the pharmaceutical field. For example, tablets or capsules contain 50 to 500 mg of compounds (I). Especially, the compounds (I) of the present invention can be used for an injection and a drop as having water soluble property.

The following examples illustrate the present invention more precisely but it is not intended to limit the present invention thereto.

EXAMPLE 1

To a suspension of 0.636 g. of 4-carbamoylimidazolium-5-olate in 15 ml. of dry pyridine was dropwise added 0.848 g. of 2-furoyl chloride at a temperature below 5° C. in $N_2$ atmosphere. After being stirred for two hours at 41°–43° C., the reaction mixture was cooled to room temperature and 0.658 g. of triethylamine was added. Then the reaction mixture was concentrated under reduced pressure. To the residue was added chloroform and then separated crystals were filtered off, washed with chloroform, toluene and diethyl ether, and dried to give 0.789 g. of 5-carbamoyl-1H-imidazole-4-yl furan-2′-carboxylate, m.p. 161°–163° C. (dec.).

Recrystallized was crude material from N,N-dimethylformamide and diisopropyl ether after washing with a small quantity of water. m.p.: 186.5° C. (dec.)

$\nu_{max}^{nujol}$ (cm$^{-1}$): 3450, 3320, 3125, 1760, 1655, 1600, 1485, 1280, 1160

| Elemental analysis: | C (%) | H (%) | N (%) |
|---|---|---|---|
| Calculated for $C_9H_7O_4N_3$ | 48.89 | 3.19 | 19.00 |
| Found | 48.8 | 3.4 | 18.8 |

EXAMPLE 2

Following a procedure similar to that of Example 1 but using 0.636 g. of 4-carbamoylimidazolium-5-olate and 0.880 g. of 2-thiophenecarbonyl chloride there was obtained 0.993 g. of 5-carbamoyl-1H-imidazole-4-yl thiophene-2′-carboxylate, m.p. 198.5°–199° C.

Recrystallized was crude material from N,N-dimethylformamide and water. m.p.: 199°–199.5° C.

$\nu_{max}^{nujol}$ (cm$^{-1}$): 3475, 3450, 3200-3100, 1730, 1670, 1605, 1460, 1380, 1265, 1120

| Elemental analysis: | C (%) | H (%) | N (%) | S (%) |
|---|---|---|---|---|
| Calculated for $C_9H_7O_3SN_3$ | 45.57 | 2.97 | 17.71 | 13.52 |
| Found | 45.36 | 2.77 | 17.94 | 13.14 |

EXAMPLE 3

Following a procedure similar to that of Example 1 but using 0.636 g. of 4-carbamoylimidazolium-5-olate, 1.157 g. of nicotinoyl chloride hydrochloride and 1.315 g. of triethylamine there was obtained 0.988 g. of 5-carbamoyl-1H-imidazole-4-yl nicotinate, m.p. 183.5° C. (charred).

$\nu_{max}^{nujol}$ (cm$^{-1}$): 3440, 3150, 1740, 1670, 1605, 1590, 1460, 1420, 1275, 1130, 1015, 725

| Elemental analysis: | C (%) | H (%) | N (%) |
|---|---|---|---|
| Calculated for $C_{10}H_8N_4O_3 \cdot 0.05H_2O$ | 51.52 | 3.50 | 24.03 |
| Found | 51.25 | 3.31 | 24.04 |

EXAMPLE 4

Following a procedure similar to that of Example 3 but using 0.636 g. of 4-carbamoylimidazolium-5-olate and 1.068 g. of isonicotinoyl chloride hydrochloride there was obtained 1.16 g. of 5-carbamoyl-1H-imidazole-4-yl isonicotinate, m.p. 186° C. (charred).

Recrystallized was crude material from dimethylsulfoxide and water. m.p.: 192.5° C. (charred).

$\nu_{max}^{nujol}$ (cm$^{-1}$): 3440, 3400-3000, 1760, 1650, 1590, 1420, 1250, 1100, 1045

| Elemental analysis: | C (%) | H (%) | N (%) |
|---|---|---|---|
| Calculated for $C_{10}H_8N_4O_3 \cdot 0.3 H_2O$ | 50.55 | 3.65 | 23.58 |
| Found | 50.8 | 3.6 | 23.5 |

EXAMPLE 5

To a suspension of 0.636 g. of 4-carbamoylimidazolium-5-olate in 15 ml of dry pyridine was slowly added 1.068 g. of isonicotinoyl chloride hydrochloride at a temperature below 5° C. in $N_2$ atmosphere. After being stirred for an hour at 41°–43° C., the reaction mixture was cooled to room temperature. Then separated crystals was filtered off, washed with pyridine, chloroform, ethyl acetate and diethyl ether, and dried to give 1.194 g. of 5-carbamoyl-1H-imidazole-4-yl isonicotinate hydrochloride.

$\nu_{max}^{nujol}$ (cm$^{-1}$): 3340, 3150-4100, 1755, 1660, 1605, 1585, 1460, 1380, 1250, 1050, 750

EXAMPLE 6

To a stirred solution of 12.5 ml of N,N-dimethylformamide in 7.5 ml of acetonitrile was added slowly 0.9 ml of oxalyl chloride in 10 ml of acetonitrile at −20° C. and stirring was continued for twenty minutes at −15° C. To the reaction mixture was slowly added 1.50 g. of N-methylpyrrole-2-carboxylic acid at −15° C. and stirring was continued for forty-five minutes at 0° C. To the reaction mixture were slowly added 1.272 g. of 4-carbamoylimidazolium-5-olate and 10 ml of pyridine at −20° C. and stirring was continued for ninety minutes at room temperature. After 200 ml of chloroform was added to the reaction mixture, separated precipitates were filtered off and the filtrate was concentrated under reduced pressure.

To the residue were added 30 ml of pyridine and 3.8 ml of triethylamine and separated precipitates were filtered off and the filtrate was concentrated under reduced pressure to give 1.17 g. of 5-carbamoyl-1H-imidazole-4-yl N-methylpyrrole-2′-carboxylate, m.p. 174° C. (dec.), which was recrystallized from ethanol, m.p. 189.5° C. (dec.).

$\nu_{max}^{nujol}$ (cm$^{-1}$): 3470, 3430, 3350, 3300, 3250, 1705, 1660, 1640, 1605, 1595, 1305, 1280, 1235, 1215, 1160, 1105, 1055, 1040, 990, 880

| Elemental analysis: | C (%) | H (%) | N (%) |
|---|---|---|---|
| Calculated for C$_{10}$H$_{10}$N$_4$O$_3$ | 51.27 | 4.30 | 23.92 |
| Found | 50.99 | 4.30 | 23.77 |

EXAMPLE 7

To a stirred solution of 12.5 ml of N,N-dimethylformamide in 7.5 ml of acetonitrile was added slowly a solution of 0.9 ml of oxalyl chloride in 10 ml of acetonitrile at −20° C. and reaction temperature was raised to 20° C. from −15° C. over a period of 30 minutes. To the reaction mixture was slowly added 1.77 g. of furan-3-carboxylic acid at −25° C. and stirring was continued for 16 hours at room temperature. To the reaction mixture were slowly added 1.272 g. of 4-carbamoylimidazolium-5-olate and 5 ml of pyridine at 0° C. and stirring was continued for four hours at room temperature. After 3.8 ml of triethylamine was added to the reaction mixture, separated precipitates were filered off. To the filtrate was added 170 ml of chloroform, then separated crystals were filtered off and dried to give 1.55 g. of 5-carbamoyl-1H-imidazole-4-yl furan-3′-carboxylate. m.p. 173° C. (dec.)

Recrystallized was crude material from methanol and water. m.p.: 198° C. (dec.)

$\nu_{max}^{nujol}$ (cm$^{-1}$): 3480, 3460, 1750, 1680, 1610, 1570, 1335, 1315, 1160, 1135, 1070

| Elemental analysis: | C (%) | H (%) | N (%) |
|---|---|---|---|
| Calculated for C$_9$H$_7$O$_4$N$_3$ | 48.87 | 3.19 | 19.00 |
| Found | 48.5 | 3.2 | 18.8 |

EXAMPLE 8

To a stirred suspension of 0.636 g. of 4-carbamoylimidazolium-5-olate in 15 ml of dry pyridine was added 0.883 g. of 5-methyl-2-thiophenecarbonyl chloride at a temperature below 5° C. in N$_2$ atmosphere. After being stirred for two hours at 41°–43° C., the reaction mixture was cooled to room temperature and then separated crystals were filtered off and dried to give 1.44 g. of white crystals.

Recrystallized was 0.815 g. of crude material from N,N-dimethylformamide and water to give 0.513 g. of 5-carbamoyl-1H-imidazole-4-yl 5′-methylthiophene-2′-carboxylate, m.p. 189.5° C. (charred).

$\nu_{max}^{nujol}$ (cm$^{-1}$): 3460, 1730, 1660, 1605

| Elemental analysis: | C (%) | H (%) | N (%) | S (%) |
|---|---|---|---|---|
| Calculated for C$_{10}$H$_9$N$_3$SO$_3$ | 47.80 | 3.61 | 16.72 | 12.76 |
| Found | 47.52 | 3.59 | 16.50 | 12.54 |

REFERENCE EXAMPLE 1

A mixture of 76.26 g. of 4-carbamoylimidazolium-5-olate, 174.31 g. of 1,1,1,3,3,3-hexamethyldisilazane, 1.59 g. of ammonium sulfate and 500 g. of dry xylene was refluxed for 4 hours. The reaction mixture was concentrated under reduced pressure and a tris-trimethylsilylated derivative of 4-carbamoylimidazolium-5-olate was obtained, m.p. 83°–86.5° C.

EXAMPLE 9

To a stirred solution of 1.718 g. of tris trimethylsilylated derivative of 4-carbamoylimidazolium-5-olate in 15 ml of dry tetrahydrofuran was dropwise added a solution of 0.733 g. of cyclohexanecarbonyl chloride in 5 ml of dry tetrahydrofuran at −50° C. under N$_2$ atmosphere. After being stirred for half an hour at −50° C., 0.48 g. of dry methanol was added to the reaction mixture. After being stirred for 30 minutes at −50° C., 0.51 g. of triethylamine was added.

The reaction mixture was heated up to room temperature and then separated crystals were filtered off, washed with tetrahydrofuran and chloroform and dried to give 0.737 g. of 5-carbamoyl-1H-imidazole-4-yl cyclohexane-1′-carboxylate. The filtrate of a tetrahydrofuran solution was concentrated and diethyl ether was added to the residue and separated crystals were filtered off, washed with diethyl ether and dried to give 0.251 g. of said product. Chloroform solution used for washing was concentrated and water was added to the residue and separated crystals were filtered off and dried to give 0.112 g. of said product.

Recrystallized was crude material from methanol, diethyl ether and n-hexane. m.p.: 172° C. (decomp.)

$\nu_{max}^{nujol}$ (cm$^{-1}$): 3490, 3100, 1780, 1675, 1615

| Elemental analysis: | C (%) | H (%) | N (%) |
|---|---|---|---|
| Calculated for C$_{11}$H$_{15}$N$_3$O$_3$ . 0.15H$_3$O | 55.06 | 6.43 | 17.51 |
| Found | 55.03 | 6.59 | 17.73 |

EXAMPLE 10

Following a procedure similar to that of Example 9 but using 0.523 g. of cyclopropanecarbonyl chloride there was obtained 0.805 g. of 5-carbamoyl-1H-imidazole-4-yl cyclopropane-1′-carboxylate, m.p. 154° C.

Recrystallized was crude material from methanol and diethyl ether. m.p.: 156.5° C. (dec.)

$\nu_{max}^{nujol}$ (cm$^{-1}$): 3460, 3270, 1775, 1760, 1670, 1605

| Elemental analysis: | C (%) | H (%) | N (%) |
|---|---|---|---|
| Calculated for C$_8$H$_9$N$_3$O$_3$ . 0.1H$_2$O | 48.78 | 4.71 | 21.33 |
| Found | 48.48 | 4.55 | 22.04 |

EXAMPLE 11

To a stirred solution of 1.718 g. of tris trimethylsilylated derivative of 4-carbamoylimidazolium-5-olate in 15 ml of dry tetrahydrofuran was dropwise added a solution of 0.933 g. of 2,2-dimethyl-3-(2-methyl-1-propenyl)-cyclopropanecarbonyl chloride in 5 ml of dry tetrahydrofuran at −50° C. in $N_2$ atmosphere. After being stirred for half an hour at −50° C., 0.32 g. of dry methanol was added to the reaction mixture. After being stirred for twenty minutes at −50° C., 0.51 g. of triethylamine was added.

The reaction mixture was heated up to room temperature and separated crystals were filtered off. The filtrate was concentrated under reduced pressure and diethyl ether was added to the residue and separated crystals were filtered off and dried to give 1,199 g. of 5-carbamoyl-1H-imidazole-4-yl 2',2'-dimethyl-3'-(2-methyl-1-propenyl)-cyclopropane-1'-carboxylate.

Recrystallized was crude material from dimethylsulfoxide and water. m.p.: 154.5° C.

$v_{max}^{nujol}$ (cm$^{-1}$): 3460, 3125, 1755, 1655, 1605

| Elemental analysis: | C (%) | H (%) | N (%) |
| --- | --- | --- | --- |
| Calculated for $C_{14}H_{19}N_3O_3$ | 60.63 | 6.91 | 15.15 |
| Found | 60.3 | 6.8 | 15.1 |

EXAMPLE 12

Following a procedure similar to that of Example 9 but using 1.138 g. of 2,2-dimethyl-3-(2,2-dichlorovinyl)-cyclopropanecarbonyl chloride there was obtained 0.670 g. of 5-carbamoyl-1H-imidazole-4-yl 2',2'-dimethyl-3'-(2,2-dichlorovinyl)cyclopropane-1'-carboxylate.

Recrystallized was crude material from dimethylsulfoxide and water. m.p.: 175°-176° C.

$v_{max}^{nujol}$ (cm$^{-1}$): 3450, 1750, 1655, 1600

| Elemental analysis: | C (%) | H (%) | N (%) | Cl (%) |
| --- | --- | --- | --- | --- |
| Calculated for $C_{12}H_{13}N_3O_3Cl_2 \cdot 0.5H_2O$ | 44.05 | 4.31 | 12.84 | 21.67 |
| Found | 43.83 | 4.09 | 12.84 | 20.57 |

EXAMPLE 13

Following a procedure similar to that of Example 9 but using 0.803 g. of 2,2,3,3-tetramethylcyclopropanecarbonyl chloride there was obtained 0.891 g. of 5-carbamoyl-1H-imidazole-4-yl 2',2',3',3'-tetramethylcyclopropane-1'-carboxylate.

Recrystallized was crude material from methanol, diethyl ether and hexane. m.p.: 172° C. (dec.)

$v_{max}^{nujol}$ (cm$^{-1}$): 3460, 3160, 1760, 1660, 1600

| Elemental analysis: | C (%) | H (%) | N (%) |
| --- | --- | --- | --- |
| Calculated for $C_{12}H_{17}N_3O_3 \cdot 0.1H_3O$ | 56.95 | 6.85 | 16.60 |
| Found | 56.80 | 6.86 | 16.68 |

EXAMPLE 14

To a stirred suspension of 0.636 g. of 4-carbamoylimidazolium-5-olate in 15 ml of dry pyridine was dropwise added 1.61 g. of 1-(p-chlorophenyl)-1-cyclopropanecarbonyl chloride at a temperature below 5° C. in $N_2$ atmosphere. After being stirred for two hours at 41°-43° C., the reaction mixture was cooled to room temperature and 0.83 g. of triethylamine was added. Then the reaction mixture was concentrated under reduced pressure. To the residue was added diethyl ether and then separated crystals were filtered off, washed with diethyl ether, water and diisopropyl ether and dried to give 1.176 g. of 5-carbamoyl-1H-imidazole-4-yl 1'-(p-chlorophenyl)cyclopropane-1'-carboxylate, m.p. 190° C. (charred).

Recrystallized was crude material from N,N-dimethylformamide and water. m.p.: 190°-191° C.

$v_{max}^{nujol}$ (cm$^{-1}$): 3450, 3125, 1740, 1650, 1600

| Elemental analysis: | C (%) | H (%) | N (%) | Cl (%) |
| --- | --- | --- | --- | --- |
| Calculated for $C_{14}H_{12}N_3O_3Cl$ | 55.00 | 3.96 | 13.74 | 11.60 |
| Found | 54.8 | 4.1 | 13.8 | 11.30 |

EXAMPLE 15

To a stirred suspension of 0.636 g. of 4-carbamoylimidazolium-5-olate in 15 ml of dry pyridine was dropwise added 1.61 g. of 1-methylcyclohexanecarbonyl chloride at a temperature below 5° C. in $N_2$ atmosphere. After being stirred for 3.5 hours at 41°-43° C., the reaction mixture was concentrated under reduced pressure. To the residue was added water and then separated crystals were filtered off, washed with diisopropyl ether and dried to give 1.06 g. of 5-carbamoyl-1H-imidazole-4-yl 1'-methylcyclohexane-1'-carboxylate, m.p. 197.5°-198° C.

Recrystallized was crude material from ethyl acetate. m.p.: 202.5°-203° C.

$v_{max}^{nujol}$ (cm$^{-1}$): 3460, 3440, 3320, 3180, 1760, 1660, 1610

| Elemental analysis: | C (%) | H (%) | N (%) |
| --- | --- | --- | --- |
| Calculated for $C_{12}H_{17}N_3O_3$ | 57.36 | 6.82 | 16.72 |
| Found | 57.3 | 6.8 | 16.6 |

EXAMPLE 16

To a stirred suspension of 2.358 g. of 4-carbamoylimidazolium-5-olate in 60 ml of dry pyridine was dropwise added 2.2 g. of 1-methylcyclopropanecarbonyl chloride at a temperature below 5° C. in $N_2$ atmosphere. After being stirred for two hours at 41°-43° C., 2.07 g. of triethylamine was added to the reaction mixture. Separated salts were filtered off and the filtrate was concentrated under reduced pressure. 2.89 g. of 5-carbamoyl-1H-imidazole-4-yl 1'-methylcyclopropane-1'-carboxylate was obtained. Purified was crude material by silica gel column chromatography.

m.p.: 173.5°-174° C.

$v_{max}^{nujol}$ (cm$^{-1}$): 3460, 3160, 1740, 1665, 1600

| Elemental analysis: | C (%) | H (%) | N (%) |
| --- | --- | --- | --- |
| Calculated for $C_9H_{11}N_3O_3 \cdot 0.1H_2O$ | 51.23 | 5.35 | 19.91 |
| Found | 51.42 | 5.38 | 19.71 |

EXAMPLE 17

Following a procedure similar to that of Example 16 but using 0.636 g. of 4-carbamoylimidazolium-5-olate, 15 ml of dry pyridine, 1.03 g. of 2,2-dichloro-1-methylcyclopropanecarbonyl chloride and 0.612 g. of triethylamine there was obtained 1.123 g. of 5-carbamoyl-1H-imidazole-4-yl 2',2'-dichloro-1'-methylcyclopropane-1'-carboxylate, m.p. 169°-172° C. (charred).

$v_{max}^{nujol}$ (cm$^{-1}$): 3460, 3320, 3150, 1760, 1680, 1600.

| Elemental analysis: | C (%) | H (%) | N (%) | Cl (%) |
|---|---|---|---|---|
| Calculated for C$_9$H$_9$N$_3$O$_3$Cl$_2$ | 38.87 | 3.26 | 15.11 | 25.50 |
| Found | 38.96 | 3.31 | 15.02 | 25.47 |

EXAMPLE 18

Following a procedure similar to that of Example 9 but using 0.593 g. of cyclobutanecarbonyl chloride there was obtained 0.752 g. of 5-carbamoyl-1H-imidazole-4-yl cyclobutane-1'-carboxylate.

Recrystallized was crude material from N,N-dimethylformamide, tetrahydrofuran, diethyl ether and hexane.

m.p.: 160° C. (dec.)

$v_{max}^{nujol}$ (cm$^{-1}$): 3430, 3320, 3150, 1740, 1670, 1605

According to the present invention, there are obtained, for example, the following compounds:

5-carbamoyl-1H-imidazole-4-yl thiophene-3'-carboxylate,
5-carbamoyl-1H-imidazole-4-yl picolinate,
5-carbamoyl-1H-imidazole-4-yl picolinate N-oxide,
5-carbamoyl-1H-imidazole-4-yl nicotinate N-oxide,
5-carbamoyl-1H-imidazole-4-yl isonicotinate N-oxide,
5-carbamoyl-1H-imidazole-4-yl pyrazine-2'-carboxylate,
5-carbamoyl-1H-imidazole-4-yl 5'-benzylfuran-3'-carboxylate,
5-carbamoyl-1H-imidazole-4-yl 6'-chloronicotinate,
5-carbamoyl-1H-imidazole-4-yl 2'-chloronicotinate,
5-carbamoyl-1H-imidazole-4-yl 5'-acetylfuran-2'-carboxylate,
5-carbamoyl-1H-imidazole-4-yl cyclopentane-1'-carboxylate,
5-carbamoyl-1H-imidazole-4-yl cycloheptane-1'-carboxylate,
5-carbamoyl-1H-imidazole-4-yl cyclooctane-1'-carboxylate,
5-carbamoyl-1H-imidazole-4-yl 1'-(p-methoxyphenyl)-cyclopentane-1'-carboxylate,
5-carbamoyl-1H-imidazole-4-yl 1'-phenylcyclopentane-1'-carboxylate,
5-carbamoyl-1H-imidazole-4-yl 1'-(p-tolyl)cyclopentane-1'-carboxylate,
5-carbamoyl-1H-imidazole-4-yl 3'-formylcyclohexane-1'-carboxylate,
5-carbamoyl-1H-imidazole-4-yl 1'-hydroxycyclohexane-1'-carboxylate,
5-carbamoyl-1H-imidazole-4-yl 1'-aminocyclopentane-1'-carboxylate,
5-carbamoyl-1H-imidazole-4-yl 2'-carboxycyclohexane-1'-carboxylate,
5-carbamoyl-1H-imidazole-4-yl 4'-aminomethylcyclohexane-1'-carboxylate,
5-carbamoyl-1H-imidazole-4-yl 3'-oxocyclopentane-1'-carboxylate,
5-carbamoyl-1H-imidazole-4-yl 1'-chloro-2'-oxocyclopentane-1'-carboxylate.

What is claimed is:
1. A compound of the formula

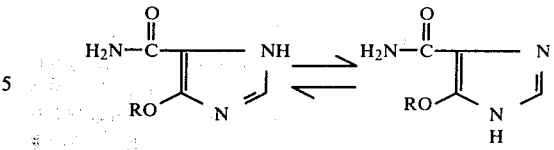

wherein R is a substituted or unsubstituted five to six membered heteroaroyl group selected from the group consisting of furancarbonyl, thiophenecarbonyl, pyrrolecarbonyl, pyridinecarbonyl, pyridinecarbonyl N-oxide, pyrazinecarbonyl, imidazolecarbonyl, pyrazolecarbonyl or thiazolecarbonyl, said substituent being selected from a lower alkyl group, a C$_{7-8}$ aralkyl group, a lower alkanoyl group, a benzoyl group or a halogen atom; or a C$_{3-8}$ cycloalkanoyl group which may be substituted with a lower alkyl group, a lower alkenyl group, a halogen atom, a halogeno-lower alkenyl group, a phenyl group, a halogeno-phenyl group, a lower alkoxyphenyl group, a lower alkylphenyl group, a formyl group, a hydroxy group, an amino group, a carboxyl group, an aminomethyl group or an oxo group, or a non-toxic salt thereof.

2. A compound according to claim 1, wherein R is a substituted or unsubstituted furancarbonyl, thiophenecarbonyl, pyrrolecarbonyl, pyridinecarbonyl, pyridinecarbonyl N-oxide, pyrazinecarbonyl, imidazolecarbonyl, pyrazolecarbonyl or thiazolecarbonyl, said substituent being selected from a lower alkyl group, a C$_{7-8}$ aralkyl group, a lower alkanoyl group, a benzoyl group or a halogen atom.

3. A compound according to claim 1, wherein R is a C$_{3-8}$ cycloalkanoyl group which may be substituted with a lower alkyl group, a lower alkenyl group, a halogen atom, a halogeno-lower alkenyl group, a phenyl group, a halogeno-phenyl group, a lower alkoxyphenyl group, a lower alkylphenyl group, a formyl group, a hydroxy group, an amino group, a carboxyl group, an aminomethyl group or an oxo group.

4. A compound according to claim 2, wherein R is 2-furancarbonyl.

5. A compound according to claim 2, wherein R is 2-thiophenecarbonyl.

6. A compound according to claim 2, wherein R is nicotinoyl.

7. A compound according to claim 2, wherein R is isonicotinoyl.

8. A compound according to claim 2, wherein R is isonicotinoyl hydrochloride.

9. A compound according to claim 2, wherein R is 3-furancarbonyl.

10. A compound according to claim 3, wherein R is 1-cyclohexanecarbonyl.

11. A compound according to claim 3, wherein R is 1-cyclopropanecarbonyl.

12. A compound according to claim 3, wherein R is 1-cyclobutanecarbonyl.

13. A compound according to claim 2, wherein R is N-methylpyrrole-2-carbonyl.

14. A compound according to claim 2, wherein R is 5-methyl-2-thiophenecarbonyl.

15. A compound according to claim 3, wherein R is 2,2-dimethyl-3-(2-methyl-1-propenyl)-1-cyclopropanecarbonyl.

16. A compound according to claim 3, wherein R is 2,2-dimethyl-3-(2,2-dichlorovinyl)-1-cyclopropanecarbonyl.

17. A compound according to claim 3, wherein R is 2,2,3,3-tetramethyl-1-cyclopropanecarbonyl.

18. A compound according to claim 3, wherein R is 1-(p-chlorophenyl)-1-cyclopropanecarbonyl.

19. A compound according to claim 3, wherein R is 1-methyl-1-cyclohexanecarbonyl.

20. A compound according to claim 3, wherein R is 1-methyl-1-cyclopropanecarbonyl.

21. A compound according to claim 3, wherein R is 2,2-dichloro-1-methyl-1-cyclopropanecarbonyl.

22. An antitumor composition which comprises an effective amount, for treating Lewis Lung Carcinoma in mice, of a compound of claim 1 as an active ingredient, and a pharmaceutically acceptable carrier or diluent.

23. An immunosuppressant composition which comprises an immunosuppressive amount of a compound of claim 1 as an active ingredient and a pharmaceutically acceptable carrier or diluent.

* * * * *